United States Patent

Fischer et al.

(10) Patent No.: US 6,681,925 B2
(45) Date of Patent: Jan. 27, 2004

(54) AUTOCLAVABLE AND RESEALABLE ENDO FILE CONTAINER

(75) Inventors: Dan E. Fischer, Sandy, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 10/028,606

(22) Filed: Dec. 19, 2001

(65) Prior Publication Data

US 2003/0111361 A1 Jun. 19, 2003

(51) Int. Cl.[7] .................. A61B 19/02; B65D 25/00; B65D 83/10; B65D 85/00
(52) U.S. Cl. .............. 206/63.5; 206/45.2; 206/369; 206/751
(58) Field of Search .............. 206/63.5, 751, 206/45.2, 210, 368, 736, 756, 758, 45.24, 207, 523, 363, 366, 369, 752, 753, 217, 370, 379, 822; 220/379, 359.1, 796, 212, 628; 215/353

(56) References Cited

U.S. PATENT DOCUMENTS

| | | | |
|---|---|---|---|
| 691,695 A | 1/1902 | Aderer et al. | |
| 1,179,890 A | * 4/1916 | Boynton et al. | 206/63.5 |
| 2,210,318 A | 8/1940 | Eckert | 21/84 |
| 2,606,708 A | * 8/1952 | Irvan | 206/45.2 |
| 3,092,443 A | 6/1963 | Dietz | 21/87 |
| 3,248,167 A | 4/1966 | Friedman | 21/84 |
| 3,451,133 A | 6/1969 | Hathaway et al. | 32/22 |
| 3,911,587 A | 10/1975 | Forrest et al. | 33/174 R |
| 4,028,810 A | 6/1977 | Vice | 32/57 |
| 4,165,562 A | 8/1979 | Sarfatti | 32/57 |
| 4,182,040 A | 1/1980 | Bechtold, Jr. | 433/77 |
| 4,191,291 A | 3/1980 | Brown | 206/369 |
| 4,212,639 A | 7/1980 | Schaffner | 433/72 |
| 4,232,784 A | 11/1980 | Hesselgren | 206/10 |
| 4,253,830 A | 3/1981 | Kazen et al. | 433/77 |
| 4,256,457 A | 3/1981 | Behring | 433/77 |
| 4,306,862 A | 12/1981 | Knox | 433/77 |
| 4,327,060 A | 4/1982 | Nisii | 422/300 |
| 4,353,694 A | 10/1982 | Pelerin | 433/77 |
| 4,382,788 A | 5/1983 | Pelerin | 433/77 |
| 4,397,395 A | 8/1983 | McKelvey | 211/60 T |
| 4,503,972 A | 3/1985 | Nelligan et al. | 206/379 |
| 4,898,276 A | 2/1990 | Georgakis | 206/369 |
| 4,936,449 A | 6/1990 | Conard et al. | 206/366 |
| 4,976,615 A | 12/1990 | Kravitz | 433/75 |
| 5,006,066 A | 4/1991 | Rouse | 433/77 |
| 5,022,858 A | 6/1991 | Castellini | 433/97 |
| 5,071,346 A | 12/1991 | Domaas | 433/77 |
| 5,150,788 A | 9/1992 | Weissman | 206/369 |
| 5,154,611 A | 10/1992 | Chen | 433/77 |
| 5,172,810 A | 12/1992 | Brewer | 206/369 |
| 5,289,919 A | 3/1994 | Fischer | 206/571 |
| 5,358,112 A | 10/1994 | Gardner | 206/369 |
| 5,433,929 A | 7/1995 | Riihimaki et al. | 422/297 |
| 5,435,979 A | 7/1995 | Miller et al. | 422/300 |
| 5,525,314 A | 6/1996 | Hurson | 422/300 |

(List continued on next page.)

Primary Examiner—Jim Foster
Assistant Examiner—Gregory Pickett
(74) Attorney, Agent, or Firm—Workman Nydegger

(57) ABSTRACT

An open-ended container for holding dental instruments includes a body and a lid. The lid is configured to close the container when the lid is placed over the open end of the container. The lid is also configured for stabilizing the container in an upright position when the lid is placed over the bottom of the container. The lid is flared and generally provides greater support to the container for standing upright than does the bottom of the container. A piece of tape is used to seal and reseal the lid on the container. A foam material (e.g., open cell foam) housed within the container is used to hold dental instruments. A disinfecting solution contained within the container disinfects any dental instruments held therein.

20 Claims, 6 Drawing Sheets

U.S. PATENT DOCUMENTS

| | | | |
|---|---|---|---|
| 5,626,227 A | 5/1997 | Wagner et al. | 206/369 |
| 5,743,734 A | 4/1998 | Heath et al. | 433/77 |
| 5,967,778 A | 10/1999 | Riitano | 433/77 |
| 6,058,636 A * | 5/2000 | Colkmire | 220/359.1 |

* cited by examiner

AUTOCLAVABLE AND RESEALABLE ENDO FILE CONTAINER

BACKGROUND OF THE INVENTION

1. The Field of the Invention

The present invention is in the field of storage containers, more particularly, storage containers configured to hold and store dental or medical instruments such as endodontic files and other tools.

2. The Relevant Technology

When engaging in dental procedures, it is important that the dental instruments employed do not introduce infection into the mouth of the patient. Avoiding the introduction of microorganisms to the area of a tooth being treated is particularly important when performing root canal therapy since infections cause significant problems in root canals.

As part of the root canal therapy, the practitioner typically employs endodontic files to remove infected material from the root canal. Endodontic files typically comprise a thin distal insertion end and a proximal gripping end held by a practitioner or inserted into mechanical instruments such as a drill. The thin distal insertion end is often a delicate flexible tip with sharp edges configured to clean the root canal.

To reduce the possibility of causing infection while performing an endodontic procedure, it is vital that the endodontic files and other dental instruments be maintained in a disinfected environment before and during use. In light of this need for sterility, a variety of different disinfecting dental instrument containers have been developed.

For example, certain containers contain magnetized inner surfaces configured for holding the metallic instruments in a desired placement, such as, for example, immersed within a sterilizing solution. One problem with magnetized containers, however, is that they may only be employed to maintain certain metal instruments. In particular, magnetic containers cannot successfully be employed to maintain a plastic instrument in a desired position. Endodontic files, for example, often include non-metallic proximal gripping ends. Furthermore, containers made from certain metals can become corroded through contact with certain disinfecting solutions. Additionally, use of metal containers can also be disadvantageous due to their relative weight and cost, which may prevent their use on a disposable basis.

Other containers include a well or reservoir for containing both a sterilizing solution and an instrument completely immersed in the solution. However, such reservoirs typically fail to maintain a portion of the dental instrument outside of the reservoir. Thus, when a practitioner desires to grasp the dental instrument, the practitioner must immerse the practitioner's fingers or another dental instrument into the sanitary solution, potentially permitting infectious material to pollute the solution.

Yet other containers are configured with complex structures containing a variety of reservoirs, ports and apertures for the placement of solution and instruments. The formation of the compartmentalized reservoirs, however, requires molding and extrusion processes that can be expensive and complex. In addition, these containers often require the dental instruments to be placed in a specific hole or in a hole selected from a specific series of holes. These containers can be inconvenient to use when it is necessary to ensure that the instruments are placed within in the appropriate holes of the container.

Another problem encountered by existing containers is that, if they are not held in an upright position, the solution within the container may spill out of the container. This is a significant problem for containers that are not very stable and that have a tendency to tip over, such as, for example containers that are tall and narrow and dimensioned to hold long, narrow dental instruments. Lids that are hingedly connected to the main storage container can be unstable. For instance, when a container is opened, by pivoting the corresponding lid to one side of the container, the container can become unbalanced and at risk of tipping over and spilling its contents.

However, if the lid is completely removed from the container when opened, it may become misplaced or lost during use. However, existing containers used to store endodontic instruments are often not configured with lids that can be attached to the containers, while simultaneously providing stability for holding the container in an upright position. This is particularly true when the container is opened, during use, which is when stability of the container is most important for preventing the contents of the container from being spilled.

Yet another problem within many existing sterilizing containers is that they do not allow a practitioner to remove debris from the instruments placed within the containers. Instead, relatively large pieces of debris may remain on the instrument when placed in a sterilizing solution, thereby hampering the sterilization process.

Accordingly, in view of the foregoing, there is currently a need in the art for improved containers configured for maintaining dental instruments in aseptic conditions. There is also a substantial need for such a container that is configured for being opened and held in a stable upright position while being connected to the lid.

SUMMARY OF PRESENTLY PREFERRED EMBODIMENTS

Briefly summarized, presently preferred embodiments of the present invention are directed to improved containers configured for holding dental instruments. The containers of the invention generally include a lid configured for closing the container during nonuse and for stabilizing the container in an upright position during use.

According to one presently preferred embodiment, the containers of the invention comprise a rectilinear body and a lid configured to be attached to the body. The body generally includes a bottom, an open ended top, and four sidewalls extending from the bottom to the open-ended top. The body is hollow and defines a cavity that is accessible through the open-ended top. The body and the lid are configured in such a manner that the lid can be securely attached to the body in two different positions. The first position is at the top of the body and the second position is at the bottom of the body.

The lid is placed in the first position over the open-ended top of the body during periods of nonuse. In the first position, the lid engages the four sidewalls and generally closes the container. According to one embodiment, the container also includes tape that is wrapped around the lid and the body in such a manner as to completely seal the container closed. The tape is preferably configured for reuse for iteratively resealing the lid to the body.

The lid is placed in the second position over the bottom of the body during periods of use. In the second position, the lid is placed upside down with the bottom of the body inserted within the lid. While in the second position, the lid engages the four sidewalls of the body and generally holds the container in an upright position. By attaching the lid to the container during use it is far less likely that the lid will be misplaced. The lid also provides stabilizing support to the container. In particular, according to one embodiment, the lid is somewhat flared so that when it is placed upside down on a planar surface the flared top of the lid provides greater surface area and increased stability to the container than would otherwise provided by the bottom of the container. The flared lid also facilitates removal of the lid from the first and second positions. The lid can also be weighted to further provide stability to the container when the lid is placed in the second position.

According to one embodiment, the container may include a foam material (e.g., an open cell foam) that is housed within the cavity and that is configured for receiving and supporting dental instruments within the cavity of the body. The structure of the foam material enables the dental instruments to be inserted within any desired portion of the cavity of the body.

According to yet another embodiment, a disinfecting solution may be contained within the container, which is advantageously absorbed within an open cell foam material or contained beneath the foam material (e.g., either an open cell or closed cell material) so that it can disinfect the dental instruments when they are inserted within the cavity of the container.

The container may also be autoclavable if desired to further provide assistance in disinfecting the dental instruments contained within the container. Examples of autoclavable materials include stainless steel, high temperature plastics, and ceramics.

In order to enable the dental practitioner to view the dental instruments without having to open the container, the lid and the body can be composed of a transparent material.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

A detailed description of the containers of the invention will now be provided with specific reference to figures illustrating preferred embodiments of the invention. It will be appreciated that like structures will be provided with like reference designations.

To provide assistance in construing the scope of the invention, definitions to terms used throughout the application will now be provided. The term "stabilize" should generally be construed as holding an object in a steady position. With specific reference to the present application, the term "stabilize" refers to holding the containers of the invention in an upright position.

The term "upright position" generally refers to the position in which the top of the container is maintained directly above the bottom of the container, wherein the "top" of the container is the portion of the container through which access to the inside of the container is provided, and wherein the bottom of the container comprises the surface or portion of the container that directly opposes the top of the container.

Briefly summarized, presently preferred embodiments of the present invention are directed to improved containers configured for holding dental instruments. The containers of the invention generally include a lid configured for closing the container during nonuse and for stabilizing the container in an upright position during use.

Figure 1:
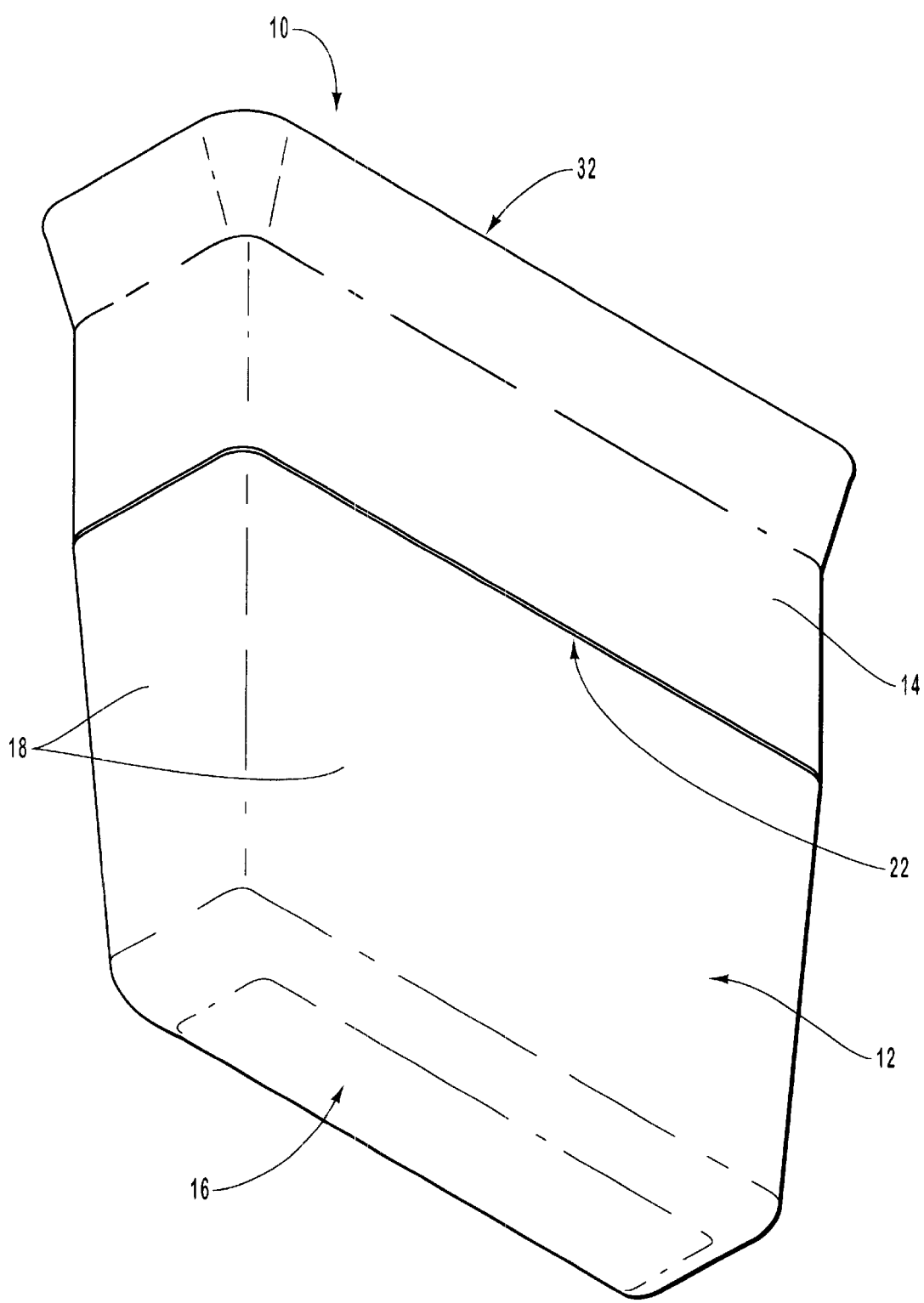
FIG. 1 illustrates a bottom perspective view of one embodiment of the container of the invention that includes a body and a lid.

Attention is first turned to FIG. 1, which illustrates one embodiment of the container 10 of the invention. As shown, the container 10 includes a body 12 and a lid 14, each of which will now be discussed in detail.

The body 12 and the lid 14 of the container 10 can be manufactured out of any desired material. Suitable nonlimiting materials include high temperature plastics, ceramic, glass, and even metal. Plastic is a particularly good material because it is relatively inexpensive, lightweight, and it is very easy to use is a variety of manufacturing processes, such as casting, injection molding, vacuum molding, blow molding, and the like. Plastic is also a very good material to use because it is easy to color, such as, for example, when manufacturing containers of different colors.

According to one embodiment, it may be useful to manufacture the containers 10 of the invention out of different colors to store different types of instruments, such as, for example, endodontic files having different shapes, flexibilities, abrasive properties, functionalities, and material compositions. This is useful because it enables the dental practitioner to readily distinguish between the differently colored containers to identify the types of instruments that are stored therein, thereby eliminating the need for the dental practitioner to read small print on the container or a label or to open the container 10 to see what is inside.

According to another embodiment, at least one of the body 12 and the lid 14 may be manufactured out of a transparent material. The use of transparent materials enables the dental practitioner to identify the types of dental instruments held within the container 10 when the container 10 holds a variety of different instruments.

According to yet another embodiment, the container 10 may be manufactured out of autoclavable materials so that the container 10 can be placed into an autoclave for sanitizing the container 10 and the dental instruments stored within the container 10. Examples of autoclavable materials include, but are not limited to, stainless steel, high temperature plastics, and ceramics.

As shown in FIG. 1, the body 12 of the container 10 includes a bottom 16 and sidewalls 18 extending upwards from the bottom. According to one embodiment, the container is rectilinear in shape and includes four sidewalls 18, although only two sidewalls are shown. The sidewalls 18 extend upwards towards an open-ended top 20 that is better illustrated in FIGS. 3 and 4. The sidewalls 18 may include a small lip 22 that extends around the circumference of the container 10, which can provide a resting or stopping point for the lid 14 when the lid 14 is placed in the closed position, as shown in FIG. 1. In the closing position, the lid 14 also slidably engages the sidewalls 18 and closes the container 10. A friction fit between the sidewalls 18 and the lid 14 may be incorporated to securely hold the lid 14 in place around the top 20 of the body 12.

Figure 2:
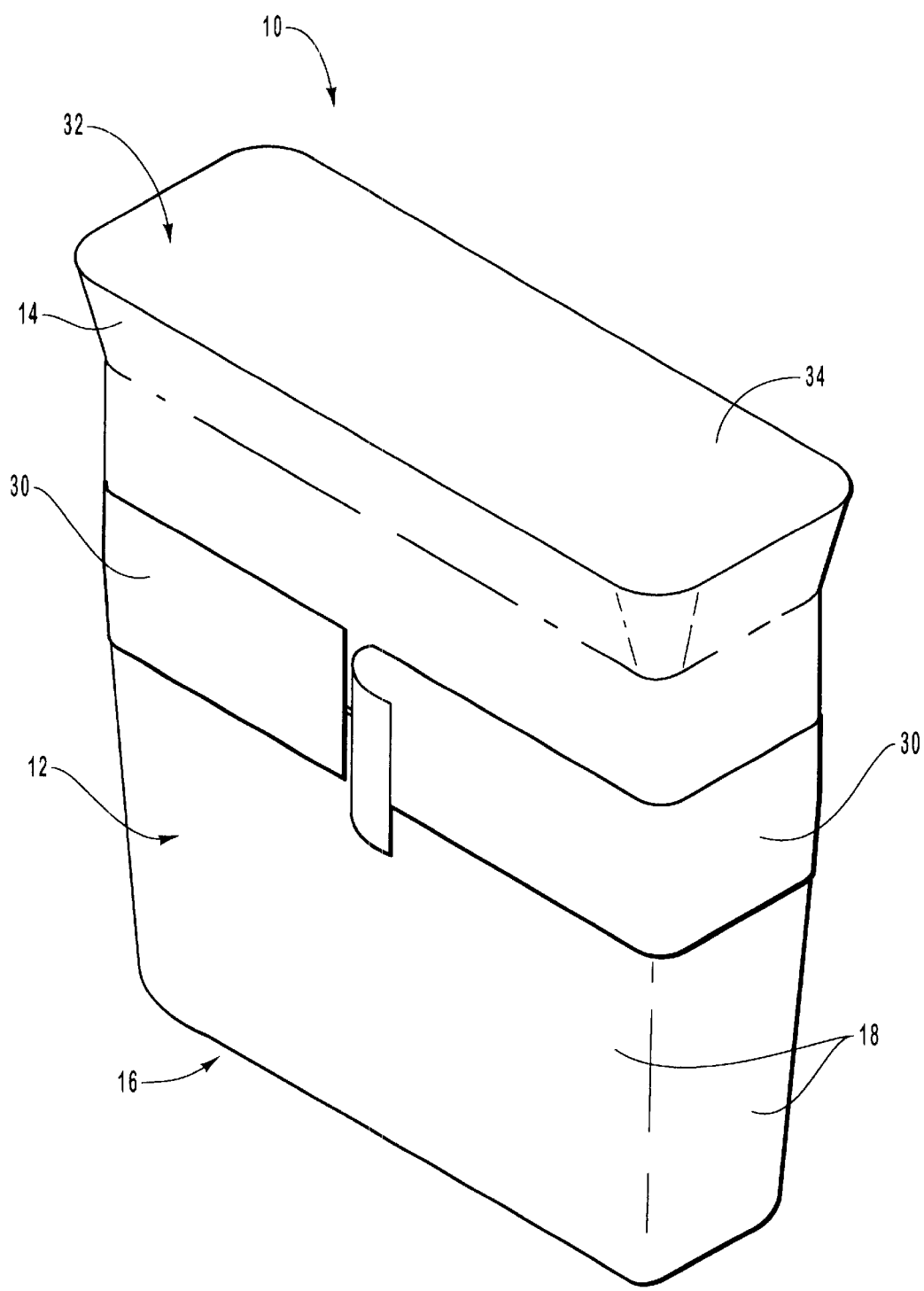
FIG. 2 illustrates a top perspective view of one embodiment of the container of the invention that includes a body, a lid, and a sealing strip wrapped around the body and the lid.

According to one embodiment, a sealing strip 30 may be provided to provide an additional restraint to hold the lid 14 onto the top 20 of the body 12. As shown in FIG. 2, sealing strip 30 (e.g., tape) can be wrapped around the circumference of the container 10 to seal the lid 14 to the body 12. This embodiment is useful for preventing the lid 14 from falling off of the body 12 when the container 10 is dropped or subjected to forces that could otherwise separate the lid from the body. Sealing strip 30 may also seal the contents of the container 10 from pathogenic invasion or oxygen and/or prevent leakage therefrom of liquids contained within the container 10.

According to one embodiment, the sealing strip 30 may be configured with means of affixation for enabling the sealing strip 30 to be reused. The sealing strip 30 may advantageously be waterproof. An example of tape having means of affixation for enabling reuse is presently sold under the name of p/n 3M/371, which is sold by 3M Industrial Packaging Division of St. Paul, Minn. It will be appreciated, however, that other types of tape can also be used with the containers of the invention, including various single-use and multi-use tapes.

FIGS. 1 and 2 also illustrate how, according to one embodiment, the lid 14 may have a flared top 32. The flared top 32 provides the lid 14 with a large cross-sectional or surface area 34 (FIG. 2) that can be used to stabilize the container 10 when the lid 14 is placed upside down beneath the container in a stabilizing position.

Figure 3:
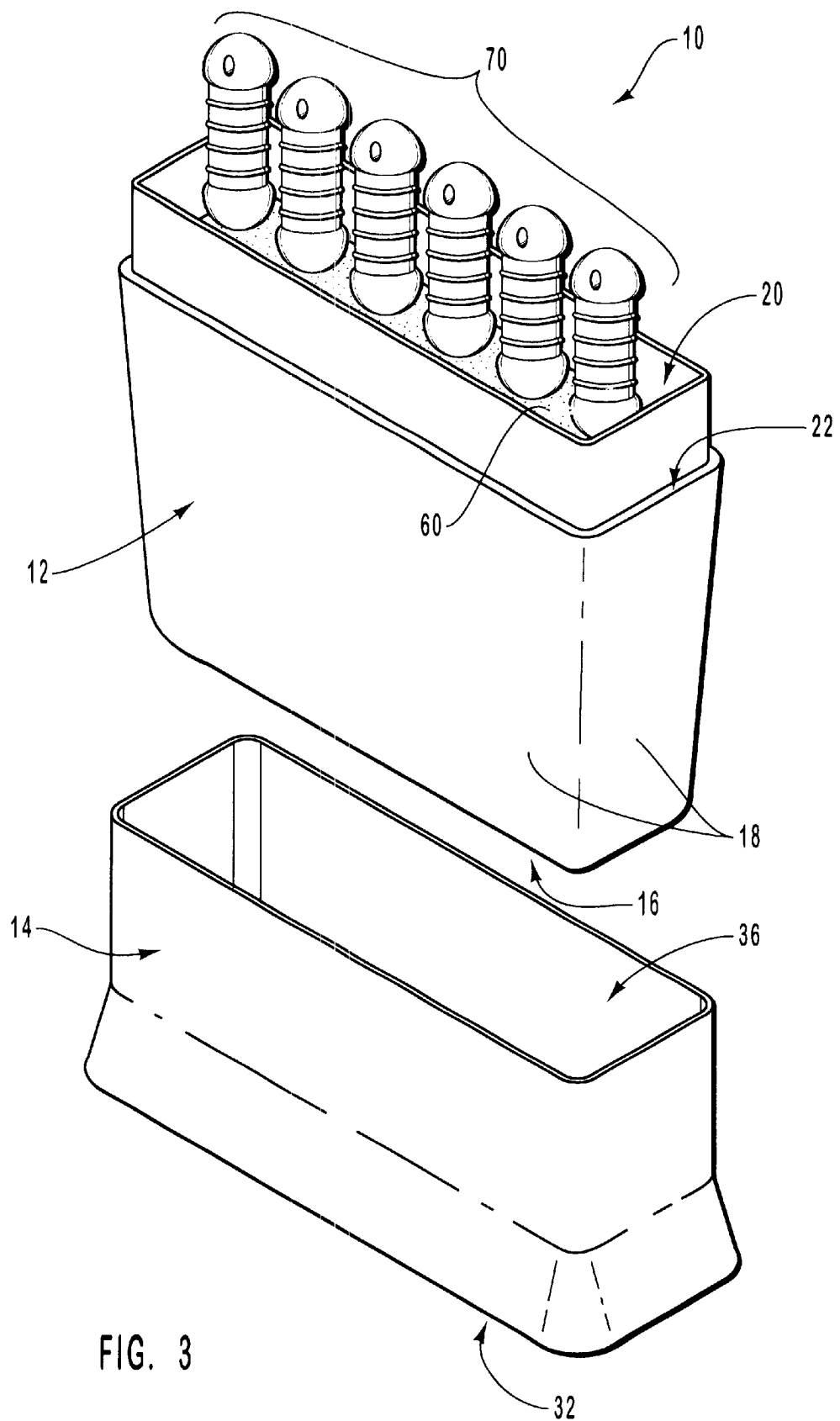
FIG. 3 illustrates on embodiment of the container of the invention that includes a body in an upright position, a lid positioned upside down beneath the body, and foam material contained within the body and holding dental instruments.
Figure 4:
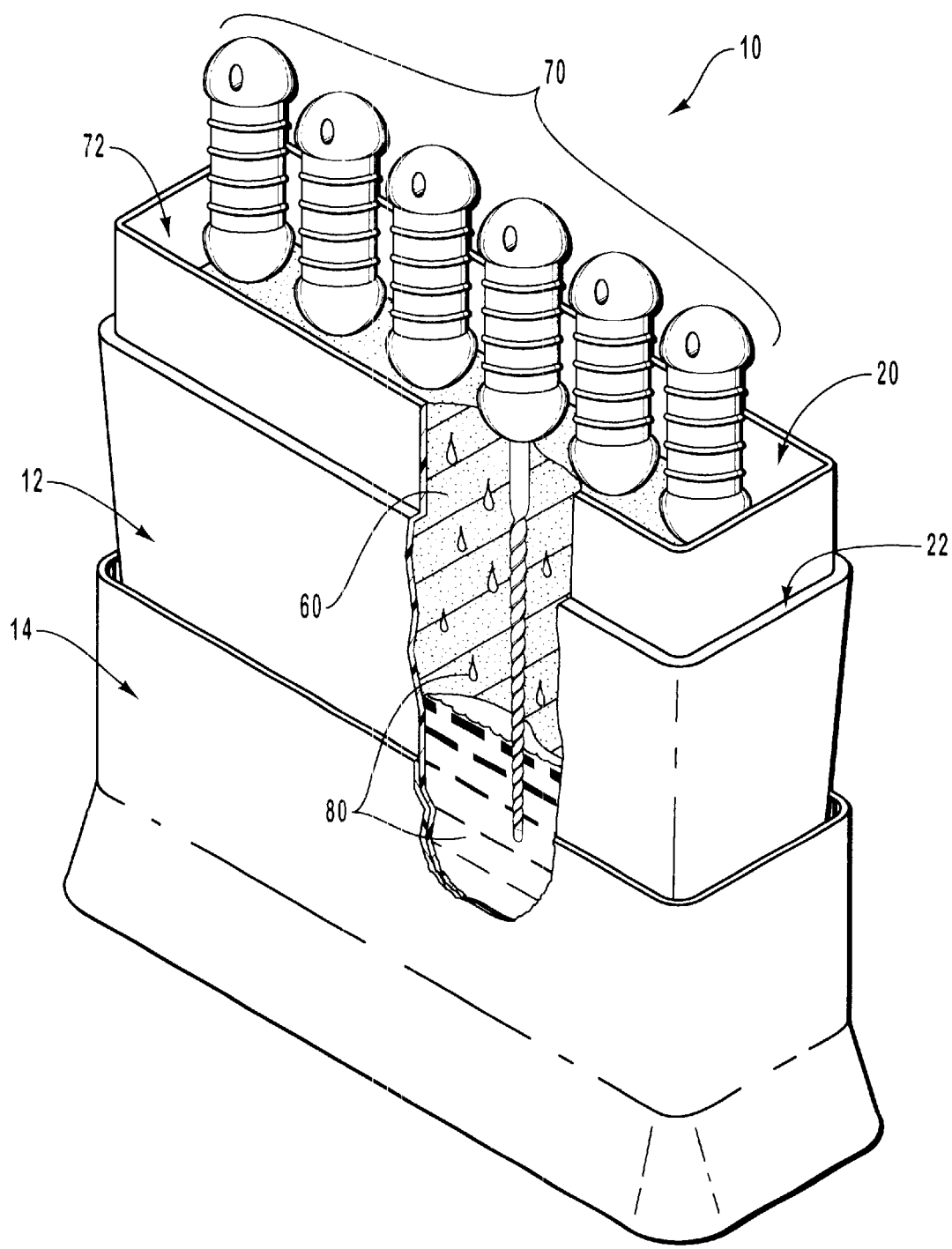
FIG. 4 illustrates a partial cross-sectional perspective view of one embodiment of the container that includes a lid placed over the bottom of a container, and a foam material and a disinfecting solution contained within the body.

FIG. 3 illustrates how the lid 14 can be positioned beneath the body 12 of the container 10 so that the bottom 16 of the body 12 can be inserted into the lid 14. As shown, the lid 14 is placed upside down, preferably on a planar surface, so that the open end 36 of the lid 14 is pointed upwards. The lid 14 is finally positioned in the stabilizing position, according to the invention, when the bottom 16 of the body 12 is inserted within the lid 14, which is configured to receive the body, as shown in FIG. 4. In the stabilizing position, the lid 14 holds the container 10 in an upright position, which may be useful for at least minimizing the risk that the container 10 will tip over. It will be appreciated that this is an improvement over the prior art containers having lids that are hingedly attached to the body.

Figure 5:
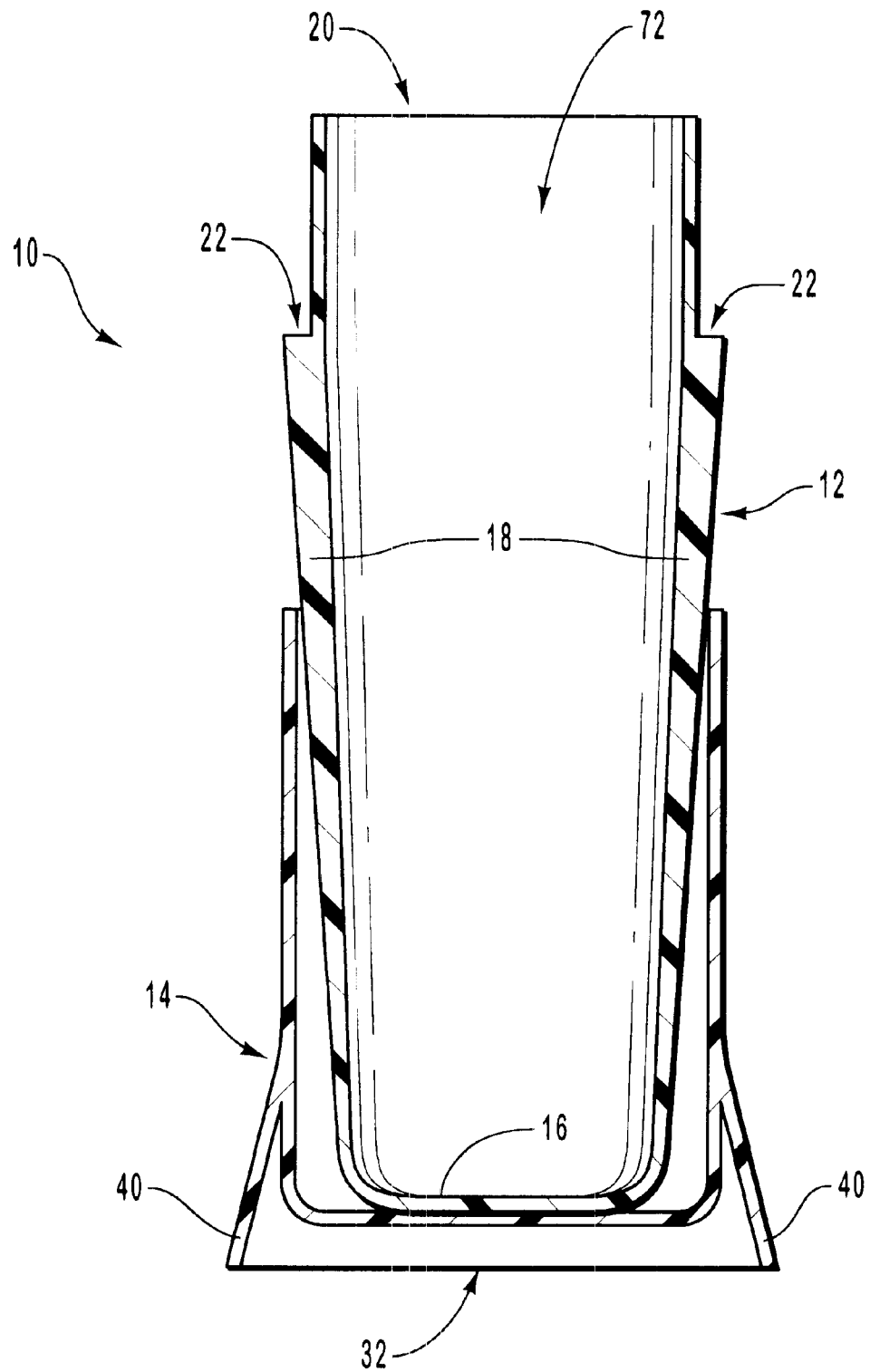
FIG. 5 illustrates a cross-sectional side view of one embodiment of the container of the invention that includes a body and a flared lid that is connected with the bottom of the body for providing support in holding the body in an upright position.

FIG. 5 illustrates a cross-sectional side view of one embodiment of the container 10 that includes a lid 14 placed in the stabilizing position so that the body 12 is held in an upright position. As shown, the lid 14 is flared for providing greater stability to the container 10 than could otherwise be provided by the bottom 16 of the body 12. In particular, the flared lid 14 provides a wider support base for stabilizing and balancing the container 10. As shown, the flares 40 of the lid 14 may independently protrude away from the lid 14. The flares 40 may also be entirely incorporated within the lid 14, as shown and described below in reference to FIG. 6.

As shown in FIG. 5, the lid 14 slidably engages the sidewalls 18 of the body 12. This creates a friction hold between the lid 14 and the sidewall 18, which is useful for keeping the lid 14 on the body 12 even when the container 10 is lifted and carried by hand. By configuring the lid 14 to be attached to the bottom 16 of the body 12, it is unlikely that the lid 14 will be misplaced or lost while the container 10 is opened. It will be appreciated that this is an improvement over the prior art containers that include lids that are not configured to be attached to the containers when opened.

Figure 6:
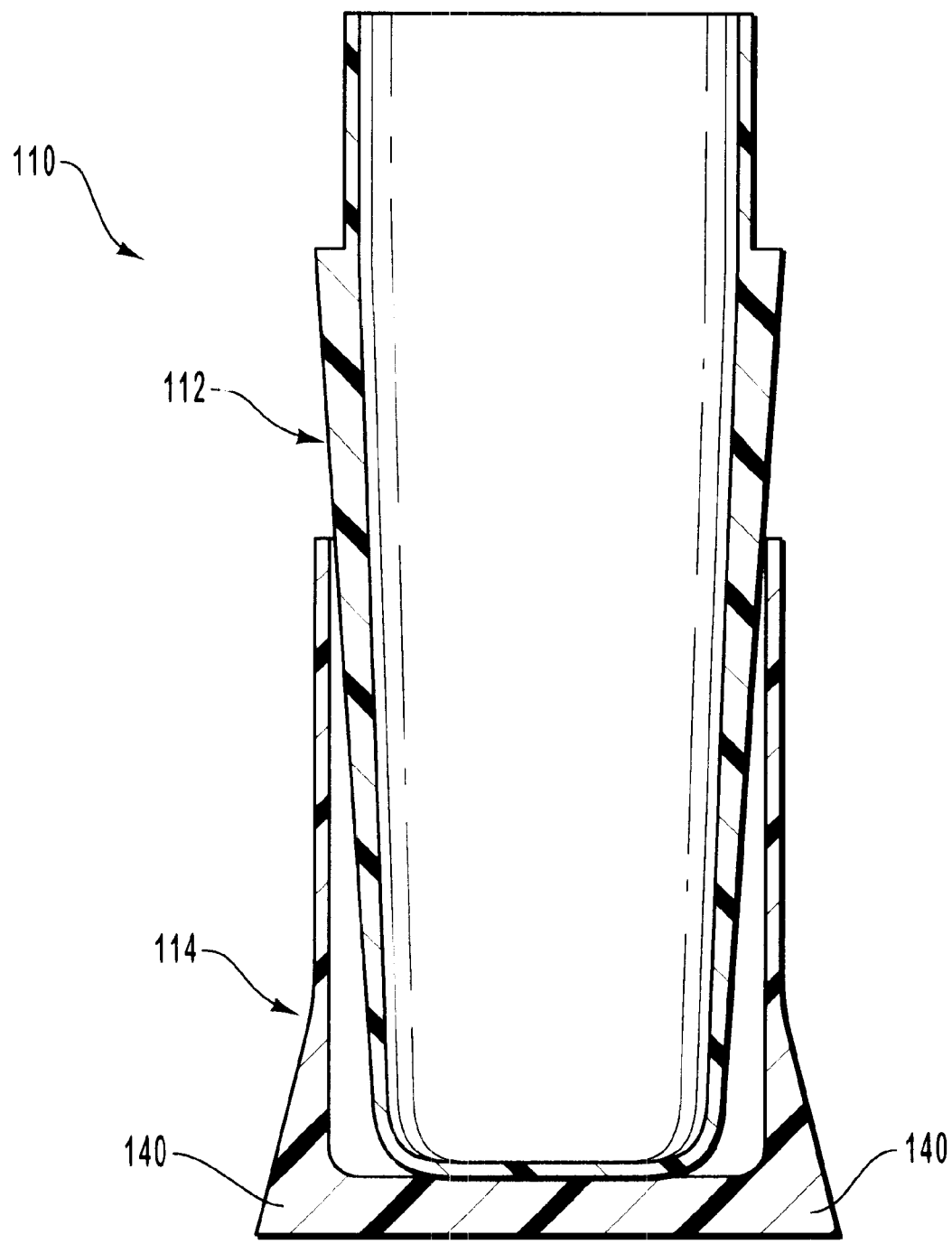
FIG. 6 illustrates a cross-sectional side view of one embodiment of the container of the invention that includes a body and a flared and weighted lid that is connected with the bottom of the body for providing support in holding the body in an upright position.

Attention is now directed to FIG. 6, which illustrates a cross-sectional side view of yet another embodiment of the container 110 of the invention. As shown, the lid 114 of the container 110 is flared, as in FIG. 5. However, instead of having flares that independently protrude away from the lid, the flares 140 are entirely incorporated within the lid 114. This embodiment can be useful for simplifying certain manufacturing processes, such as, for example, injection molding and casting of the lid 114. This embodiment is also useful for increasing the weight of the lid 114, which increases the ability of the lid 114 to stabilize the container 110. In particular, the increased weight of the lid 114 compared to lid 14 of FIG. 5 can help prevent the container 110 from tipping over when the lid 114 is placed in the stabilizing position shown.

Returning now to FIG. 3, it is shown how, according to one embodiment, the container 10 can be configured to include a support material 60 for supporting and holding one or more dental instruments 70 within the container. The support material 60 preferably has sufficient porosity and/or deformability to enable the instruments 70 to be inserted into the support material 60 without bending, blunting or otherwise damaging the instruments 70. The support material 60 may advantageously be sufficiently elastomeric or resilient to allow the support material 60 to substantially return to its original configuration when the instruments 70 are removed from the container 10 so that the instruments 70 can be repeatedly inserted into the support material 60 and be supported by the support material 60 after reinsertion.

A variety of different support materials 60 may be employed by the invention, including foam materials. Foam materials are particularly good materials because they have sufficient porosity for easy insertion of the dental instruments. Nonlimiting examples of foam materials include polymeric foam, foam rubber, and styrofoam. While naturally occurring foam materials such as a sponge can be used, synthetic foam materials are generally preferred. Other suitable synthetic materials can also be used, including plastic mesh or strands of intertwined plastic, such as nylon. Intertwined metal strands, such as steel wool, can also be used.

The support material 60 may be of any size, shape or density that enables the support material 60 to be disposed within the cavity 20 of the container 10 and to support instruments 70 within the container 10. The support material 60 may be attached to the container with any means of affixation, including, but not limited to, adhesives, chemical bonding, welding and compression fit. The support material 60 is advantageously held in place by a friction fit between the support material 60 and the sidewalls 18 of the container 10. One or more protrusions (not shown) may extend from the sidewalls 18 and into the cavity 70 of the body 12 in order to hold or retain the support material 60 in place.

Turning now to FIG. 4, it is shown how the container 10 can also be configured to include a solution 80 that is disposed within the cavity 20 of the body 12. The solution 80 preferably comprises a disinfecting solution capable of disinfecting the dental instruments 70 between uses. The solution 80 may be contained within the support material 60 or beneath the support material 60.

It will be appreciated that the containers of the invention, as they have been described, provide advantages over the containers of the prior art. One advantage of the containers of the invention is that they include lids that can be attached to the bottom of the containers for stabilizing the container, while the container is opened and in an upright position.

Although specific examples of the invention have been provided in which the containers of the invention are configured for storing endodontic instruments, it will be appreciated that the containers of the invention can also be used to store other types of dental and medical instruments that are to be maintained in a sanitary environment.

Accordingly, it will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A container configured for holding dental instruments, the container comprising:
    a body including a bottom and a plurality of sidewalls extending upwards from the bottom, the sidewalls defining a cavity and an open-ended top, the bottom being configured to rest on a planar surface;
    a support material disposed within the cavity that is configured for supporting and holding one or more dental instruments, the suPport material having sufficient porosity or deformability to enable a dental instrument to be inserted into the support material without bending, blunting or damaging the dental instrument;
    a disinfecting solution disposed within the cavity for disinfecting a dental instrument inserted into the cavity; and
    a lid configured for closing the open-ended top when the lid is placed in a closing position over the open-ended top and for stabilizing the body in an upright position when the lid is placed in a stabilizing position over the bottom of the body,
        the lid comprising an open end configured to receive and slidably engage a portion of the sidewalls when the lid is in the closing position and to receive the bottom of the body when the lid is in the stabilizing position, and
        the lid comprising an enlarged top that is significantly larger than the open end of the lid, the open-ended top of the body, and the bottom of the body and that is configured to rest on a planar surface, the enlarged top of the lid thereby providing greater stability for the container when the lid is in the stabilizing position than when the bottom of the body rests on a surface without the lid or when the bottom of the body is attached to a lid that does not have an enlarged top.

2. A container as recited in claim 1, wherein the enlarged top of the lid is flared to facilitate gripping of the lid when the lid is moved from the body.

3. A container as recited in claim 2, wherein the flared top has a planar surface.

4. A container as recited in claim 1, the support material comprising a foam material.

5. A container as recited in claim 4, further comprising one or more dental instruments held by the foam material within the cavity of the body.

6. A container as recited in claim 1, further comprising a sealing strip configured for sealing the lid to the body.

7. A container as recited in claim 6, wherein the sealing strip is configured for iteratively resealing the lid to the body.

8. A container as recited in claim 1, wherein the container comprises an autoclavable material.

9. A container as recited in claim 1, wherein at least one of the lid and the body is transparent.

10. A container as recited in claim 1, wherein the bottom of the container and the open top of the container are substantially rectilinear.

11. A container configured for holding endodontic instruments, the container comprising:
    a body including a bottom and a plurality of sidewalls extending upwards from the bottom to an open-ended top, the sidewalls defining a cavity and the open-ended top, the bottom being configured to rest on a planar surface; and
    a lid comprising an open end configured for slidably engaging the sidewalls of the body when the lid is placed in a closing position over the open-ended top, wherein the open end of the lid is further configured for slidably engaging the sidewalls of the body when the lid is placed in a stabilizing position over the bottom of the body,
        wherein the lid has an enlarged top that is significantly larger than the open end of the lid, the open-ended top of the body, and the bottom of the body and is configured to rest on a planar surface,
        the enlarged top of the lid thereby providing greater stability for the container, and preventing inadvertant spillage of liquid contained in the body cavity, when the lid is in the stabilizing position than when the bottom of the body rests on a surface without the lid or when the bottom of the body is attached to a lid that does not have an enlarged top; and
    a support material housed within the cavity of the body that is configured for supporting and holding one or more endodontic instruments securely in place within the cavity of the body, the support material having sufficient porosity or deformability to enable an endodontic instrument to be inserted into the support material without bending, blunting or damaging the endodontic instrument.

12. A container as recited in claim 11, wherein the lid comprises a flared top configured for stabilizing the body in an upright position when the lid is placed over the bottom of the body.

13. A container as recited in claim 11, further comprising a disinfecting solution contained within the support material for disinfecting dental instruments that are held in place by the support material.

14. A container for holding dental instruments, comprising:
   a body including a bottom and a plurality of sidewalls extending upwards from the bottom, the sidewalls defining a cavity and an open-ended top, the bottom being configured to rest on a planar surface;
   a lid having a flared top, the lid comprising an open end configured for slidably engaging the sidewalls of the body when the lid is placed in a closing position over the open-ended top of the body, and wherein the open end of the lid is further configured for slidably engaging the sidewalls of the body when the lid is placed in a stabilizing position over the bottom of the body;
   wherein the flared top of the lid is significantly larger than the open end of the lid, the open-ended top of the body, and the bottom of the body and is configured to rest on a planar surface,
   the flared top thereby providing greater stability for the container, and preventing inadvertant spillage of liquid contained in the body cavity, when the lid is in the stabilizing position than when the bottom of the body rests on a surface without the lid or when the bottom of the body is attached to a lid that does not have an enlarged top; and
   a support material housed within the cavity of the body that is configured for supporting and holding one or more dental instruments, the support material having sufficient porosity or deformability to enable a dental instrument to be inserted into the support material without bending, blunting or damaging the dental instrument;

15. A container as recited in claim 14, wherein the container comprises an autoclavable material.

16. A container as recited in claim 14, further comprising tape configured to seal the lid to the body.

17. A container as recited in claim 1, further comprising one or more endodontic instruments at least partially disposed within the body cavity and held in place by the support material.

18. A container as recited in claim 11, further comprising one or more endodontic instruments at least partially disposed within the body cavity and held in place by the support material.

19. A container as recited in claim 14, further comprising one or more dental instruments at least partially disposed within the body cavity and held in place by the support material.

20. A container as recited in claim 19, wherein the support material comprises a foam material and a disinfecting solution contained therein.

* * * * *

UNITED STATES PATENT AND TRADEMARK OFFICE
CERTIFICATE OF CORRECTION

PATENT NO. : 6,681,925 B2
DATED : January 27, 2004
INVENTOR(S) : Fischer et al.

It is certified that error appears in the above-identified patent and that said Letters Patent is hereby corrected as shown below:

Column 1,
Line 66, after "within" please delete "in"

Column 3,
Line 9, after "otherwise" please insert -- be --
Line 62, please delete "on" and replace with -- one --

Column 4,
Line 52, please delete "is" and replace with -- in --

Column 7,
Line 51, please delete "suPport" and replace with -- support --

Column 10,
Line 7, please delete ";" and replace with -- . --

Signed and Sealed this

Twenty-fourth Day of August, 2004

JON W. DUDAS
*Director of the United States Patent and Trademark Office*